July 21, 1964 P. E. GIRARD Plant Pat. 2,427
SORBARONIA HYBRIDA PLANT
Filed June 15, 1962
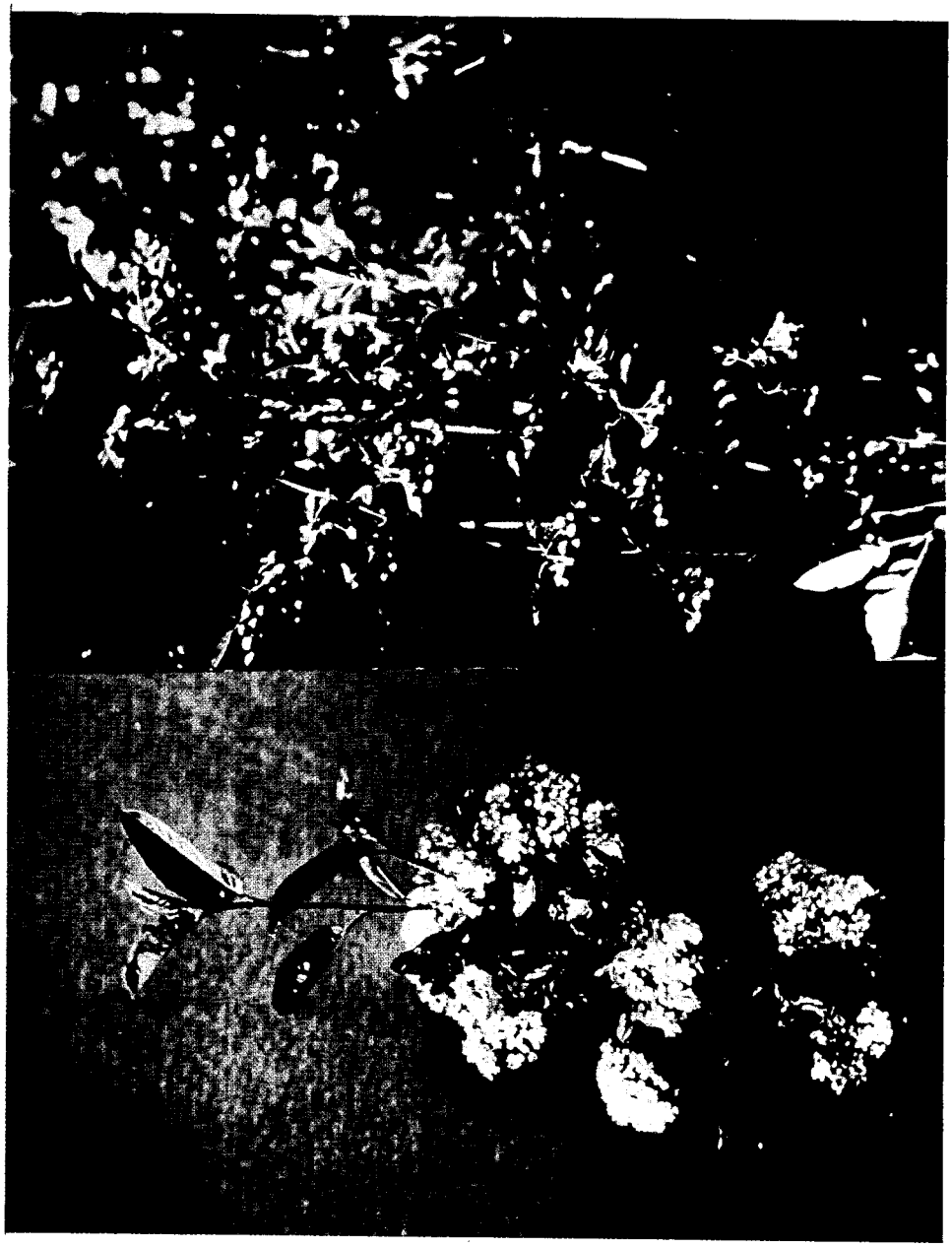
INVENTOR
PETER E. GIRARD
BY
Fay & Fay
ATTORNEYS United States Patent Office Plant Pat. 2,427
Patented July 21, 1964

2,427
*SORBARONIA HYBRIDA* PLANT
Peter E. Girard, Geneva, Ohio
Filed June 15, 1962, Ser. No. 202,927
1 Claim. (Cl. Plt.—51)

The present invention relates to a new and distinct variety of ornamental tree.

The original plant was discovered accidentally in 1954 and is a hybrid seedling which was propagated in a chance manner from a European mountain ash, i.e. *Sorbus aucuparia,* which was grown next to an *Aronia arbutifolia brilliantissima.* The seed from this plant was collected and propagated. However, it will not come true from seedlings but has been propagated by budding, grafting, and cuttings.

This new plant is characterized by heavy, white flowering in May and rich purplish wine-red berries in the late summer and fall, and by deep green foliage that is lustrous and heavy. The flowering in the spring appears on all of the branchlets, replaced by numerous clusters of wine-red berries in the fall. The characteristics of the plant are described in further detail, as follows:

*Parentage.*—A chance hybrid seedling of a European mountain ash which was grown next to an *Aronia arbutifolia brilliantissima.*

*Propagation.*—Seedlings will not come true, but the plant has been propagated readily by budding, grafting, and cuttings. It has been asexually reproduced by applicant, by budding, grafting, and cuttings, at a nursery in Geneva, Ohio. Such plants mature to about 3–4 feet in height in the first year.

*Location (where grown).*—Plants will grow in most type soils, and in moderate, temperate climate, i.e. zone 5 climate. They will withstand colder weather and probably will grow in zone 3 or zone 4 climate. There has not been any experience of winter injury during the propagation up to the present time.

*Growth habits.*—The plant has shown vigorous growth. It forms a very dense head and is generally upright; when cut back it can be grown into a dense hedge. The tree probably will mature to 25–30 feet in time.

*The tree.*—The size of the tree is now 8–10 feet in height. Since the original seedling was injured in cultivation and subsequent cuttings were topped for further propagation, full growth for the period has not been experienced. The plant is generally upright with many small branches and branchlets causing a dense appearance. The trunk is smooth and shiny and of a light brown color. It is redder than a mountain ash; in fact is nearly reddish brown.

*Leaves.*—They are of two types: simple ovate leaves with serrate margins, which are 2½″ to 3″ long and 1½″ to 2″ wide; the compound leaves are up to 8″ long and resemble those of the mountain ash. These compound leaves vary from 3 or 4 leaflets, to as many as 7. They have serrated edges and are lanceolate or oval in shape. The simple ovate leaves usually are closer to the central stem while the compound, lanceolate-leaflets are inclined to be further along the stem, progressing toward the tip. The color is a lustrous, deep green (plate 23E12) with a heavy texture and a slight pubescence beneath the leaf.

*Flowers.*—The plant blooms early, about the first to the tenth of May in the northern Ohio climate, and has approximately the same blooming time as the *Sorbus aucuparia.* The blossoms are milk white to pure white upon first opening (Plate 26A1), and are relatively long lasting and frost resistant. Each petal is about ⅛″ in diameter—the florets about 7/16″ in diameter. There are as many ac 75–100 florets in one cluster and instead of being flat, as in the mountain ash, they are rounded clusters. The flowering characteristics are defined further by the fact that each branchlet has blooms, as seen in the drawings, and the flowers are not confined to the very ends of the branch, as in the mountain ash. The plant produces very heavy flowering.

*Berries.*—The berries are heavy, full, spherical to subglobose and a rich wine-red (Plate 45L9; they are somewhat smaller than the berries of the mountain ash but are much more profuse. They start to color a rich purplish red in late summer and hold on well into the winter.

*Foliage.*—The foliage is a deep, lustrous green and quite shiny. In the fall some copper and purple shading occurs. The plant is hardy and the foliage holds well, but it is not an evergreen.

Plate identifications used above refer to Maerz and Paul Dictionary of Color.

The *Sorbaronia hybrida* plant described herein is believed to be superior to existing similar varieties because of its ability to bloom profusely; because of its lustrous, deep green foliage of very heavy texture; and because of the abundant clusters of berries which start to color a rich, purplish red in late summer and hold on well into the winter. It is an ideal tree for ornamental use; it will attract much attention when in bloom in the spring, and when in fruit in the fall; and its foliage is attractive throughout the summer.

I claim:

A new and distinct variety of *Sorbaronia hybrida* plant, an ornamental tree as described and illustrated, characterized particularly as to novelty by its vigorour growth habits; its deep, lustrous green foliage; its numerous clusters of creamy white to milky white flowers having 75–100 florets in each rounded cluster; its numerous purplish wine-red berries; its upright growth habits; and its easy propagation by budding, grafting, or cuttings.

No references cited.